United States Patent
Jäger et al.

[11] Patent Number: 4,758,582
[45] Date of Patent: Jul. 19, 1988

[54] NOVEL AZOLYL-AROXYMETHYL-DIMETHYLPENTYNOL FUNGICIDES

[75] Inventors: Gerhard Jäger, Leverkusen; Manfred Jautelat, Burscheid; Dieter Arlt, Cologne; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 816,540

[22] Filed: Jan. 6, 1986

[30] Foreign Application Priority Data

Jan. 16, 1985 [DE] Fed. Rep. of Germany ....... 3501245

[51] Int. Cl.$^4$ .................. A01N 43/653; C07D 249/08
[52] U.S. Cl. .................................. 514/383; 514/184; 514/399; 548/101; 548/262; 548/341; 549/555
[58] Field of Search ................ 548/101, 262; 514/184, 514/383

[56] References Cited

U.S. PATENT DOCUMENTS

| | | | |
|---|---|---|---|
| 4,505,922 | 3/1985 | Jager et al. | 548/262 |
| 4,507,140 | 3/1985 | Sugavanam | 548/262 |
| 4,554,285 | 11/1985 | Zech et al. | 548/262 |
| 4,578,396 | 3/1986 | Jager et al. | 548/262 |
| 4,655,820 | 4/1987 | Worthington et al. | 548/262 |

FOREIGN PATENT DOCUMENTS

| | | | |
|---|---|---|---|
| 0073331 | 3/1983 | European Pat. Off. | 548/262 |
| 0084834 | 8/1983 | European Pat. Off. | 548/262 |
| 0110048 | 6/1984 | European Pat. Off. | 548/262 |
| 0123160 | 10/1984 | European Pat. Off. | 548/262 |
| 0129798 | 1/1985 | European Pat. Off. | 548/262 |
| 3222166 | 12/1983 | Fed. Rep. of Germany | 548/262 |

*Primary Examiner*—Glennon H. Hollrah
*Assistant Examiner*—Patricia L. Morris
*Attorney, Agent, or Firm*—Sprung Horn Kramer & Woods

[57] ABSTRACT

Novel fungicidally active compounds of the formula

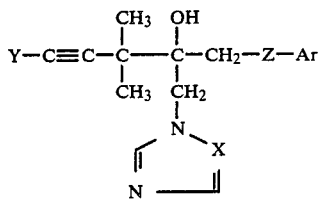

in which
X is nitrogen or the CH group,
Y is hydrogen, bromine or iodine,
Z is oxygen, sulphur, the —SO— group or the —SO$_2$— group, and
AR is optionally substituted aryl, or physiologically tolerated additon products thereof with acids or metal salts.

9 Claims, No Drawings

NOVEL AZOLYL-AROXYMETHYL-DIMETHYLPENTYNOL FUNGICIDES

The present invention relates to novel azolyl-aroxymethyl-dimethylpentinols, to a process for their preparation and to their use as fungicides.

It has already been disclosed that substituted 1-hydroxyalkyl-azolyl derivatives possess fungicidal properties (compare, for example, EP-A No. 0,084,834. The action of these compounds is however not always fully satisfactory, especially when low concentrations are used.

There have now been found the new azolyl-aroxymethyl-dimethylpentinols of the general formula (I)

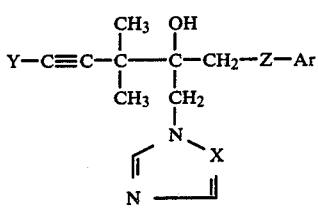

in which
X represents nitrogen and the CH group,
Y represents hydrogen, bromine and iodine,
Z represents oxygen, sulphur, the —SO— group and the —SO$_2$— group and
Ar represents optionally substituted aryl, and their physiologically tolerated acid addition salts and metal salt complexes.

The azolyl-aroxymethyl-dimethylpentinols of the formula (I)

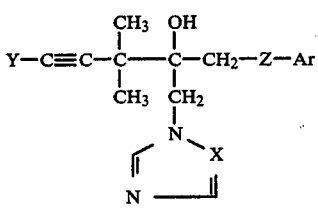

in which
X represents nitrogen and the CH group,
Y represents hydrogen, bromine and iodine,
Z represents oxygen, sulphur, the —SO— group and the —SO$_2$— group and
Ar represents optionally substituted aryl, and their physiologically tolerated acid addition salts and metal salt complexes, are obtained when oxirane derivatives of the formula (II)

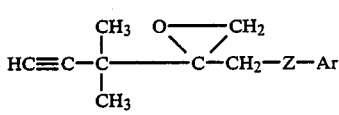

in which
Z and Ar have the abovementioned meaning are reacted with azoles of the formula (III)

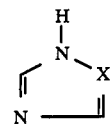

in which
X has the abovementioned meaning if appropriate in the presence of a diluent and of a base and, if appropriate, the thus obtained compounds of the formula (Ia) (namely those compounds of the general formula (I) in which Y represents hydrogen)

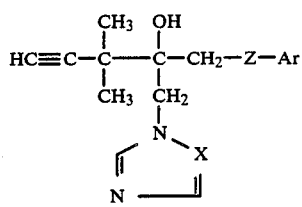

in which
X, Z and Ar have the abovementioned meaning, are halogenated with bromine or iodine, if appropriate in the presence of a diluent and of an acid acceptor, and furthermore, if appropriate, the resulting compounds of the general formula (I) are subjected to an addition reaction with an acid or a metal salt.

The new azolyl-aroxymethyl-dimethylpentinols of the formula (I) exhibit powerful fungicidal properties. Surprisingly, the compounds according to the invention show a substantially more powerful fungicidal action than the 1-hydroxyalkyl-azolyl derivatives known from the state of the art. Accordingly, the new compounds constitute an enrichment of the state of the art.

Preferred compounds according to the invention, of the formula (I), are those in which
Ar represents phenyl and naphthyl, it being possible for the said radicals to be substituted by halogen, by alkyl, alkoxy and alkylthio each with up to 4 carbon atoms, by halogenoalkyl, halogenoalkoxy and halogenoalkylthio each with up to 2 carbon atoms and up to 5 halogen atoms, by optionally halogen-substituted phenyl or phenoxy and, finally, by the groups CH$_3$—O—N=CH— and CH$_3$—O—N=C(CH$_3$)—, and
X, Y and Z have the meaning given in the definition of the invention.

Particularly preferred compounds of the general formula (I) are those in which
Ar represents phenyl which is optionally monosubstituted, disubstituted or trisubstituted by fluorine and chlorine, by methyl, ethyl and isopropyl, by halogenomethyl with 1 to 3 fluorine or chlorine atoms, by methoxy, methylthio, trifluoromethoxy and trifluoromethylthio and/or by the groups CH$_3$—O—N=CH— and CH$_3$—O—N=C(CH$_3$)— as well as monosubstituted by phenyl or phenoxy, the two last-mentioned radicals, in turn, being optionally monosubstituted, disubstituted or trisubstituted by fluorine and chlorine, and
X, Y and Z have the meaning given in the definition of the invention.

Specifically, the following compounds of the general formula (I) may be mentioned as examples, in addition to the compounds mentioned in the preparation examples:

| X | Y | Z | Ar |
|---|---|---|---|
| CH | H | O | 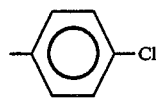 |
| CH | I | O | 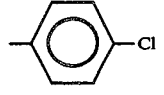 |
| CH | H | O | 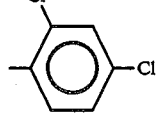 |
| CH | I | O | 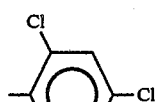 |
| CH | H | O |  |
| CH | I | O | 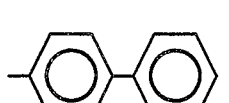 |
| CH | Br | O |  |
| CH | H | O | 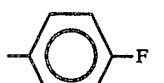 |
| CH | I | O | 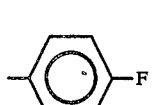 |
| CH | H | S | 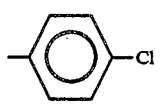 |
| CH | I | S | 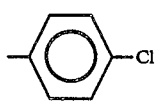 |
| N | H | S | 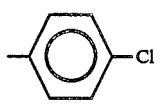 |
| N | I | S | 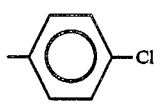 |
-continued
| X | Y | Z | Ar |
|---|---|---|---|
| N | H | S | 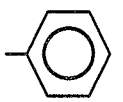 |
| N | I | S |  |
| N | H | SO | 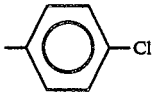 |
| N | H | SO$_2$ | 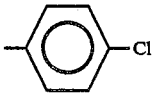 |
| N | I | SO$_2$ | 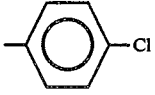 |
| N | I | O | 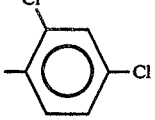 |
| N | Br | O | 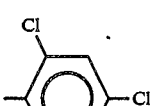 |
| N | Br | O | 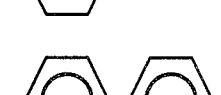 |
| N | I | O |  |
| N | H | O |  |
| N | I | O |  |
| N | H | O | 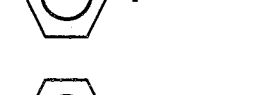 |
| N | I | O |  |

-continued

| X | Y | Z | Ar |
|---|---|---|---|
| N | H | O | -C₆H₄-C(CH₃)=N-OCH₃ |
| N | H | O | -C₆H₄-CF₃ |
| N | I | O | -C₆H₄-CF₃ |
| N | H | O | -C₆H₄-O-CF₃ |
| N | H | O | -C₆H₄-S-CF₃ |
| N | H | O | -C₆H₄-O-C₆H₅ |

If, for example, 2-(4-chlorophenoxymethyl)-2-(3-methyl-1-butin-3-yl)-oxirane and 1,2,4-triazole are used as starting materials, in the presence of sodium butanolate, for the preparation of the compounds according to the invention, of the formula (I), the course of the reaction can be represented by the following equation:

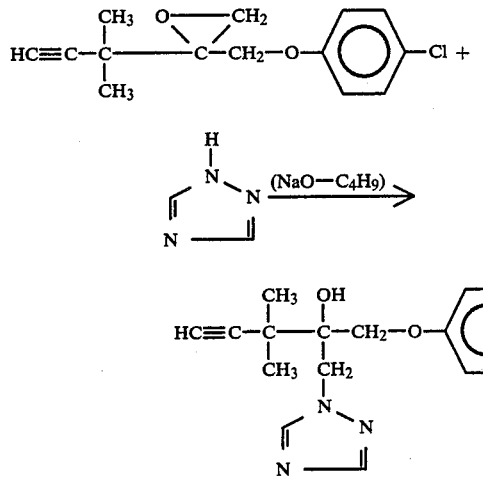

If, the compound thus obtained is halogenated, for example with iodine in the presence of sodium hydroxide solution, then this can be represented as follows:

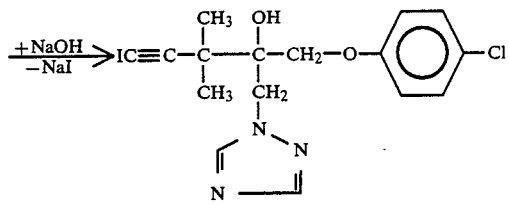

The oxirane derivatives to be used as starting materials are defined by the general formula (II). In this formula, Z and Ar preferably have the meanings which have already been mentioned as preferred for these substituents when discussing the compounds of the formula (I).

The oxirane derivatives of the formula (II) can be prepared in accordance with generally known methods (see, in this context, EP-A No. 0,084,835. Thus, for example, the corresponding ketones of the formula (IV)

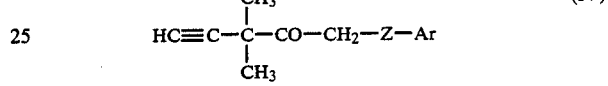

in which

Z and Ar have the abovementioned meaning, can either (a) be reacted with dimethyloxosulphonium methylide in the presence of a suitable diluent, such as, for example, dimethylsulphoxide, in the temperature range between +20° and 80° C., or (b) be reacted with trimethylsulphonium methyl-sulphate in the presence of an inert organic solvent, such as, for example, acetonitrile, and in the presence of a base, such as, for example, sodium methylate, in the temperature range between 0° and 60° C. (compare, in this context, the cited EP-A and the data in J. Amer. Chem. Soc. 87, pages 1363-1364 (1965), which include further details).

The ketones of the formula (IV) are also obtained in a known manner, by reacting 1-chloro-3,3-dimethyl-4-pentin-2-one of the formula (V)

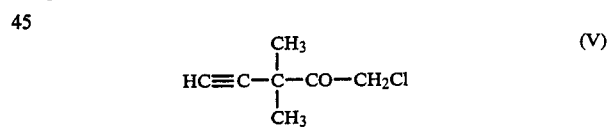

with phenols or thiophenols in the presence of an acid acceptor, such as potassium carbonate, and a diluent, such as acetone, in the temperature range between +40° and 100° C. (the known Williamson ether synthesis). The compounds thus obtained, of the formula (VI)

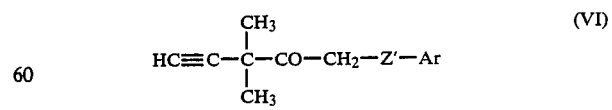

in which

Z' represents oxygen or sulphur and

Ar has the meanings given above, can, in the case of the sulphur compounds, be further converted to the sulphoxide and sulphone stages. This is done in a generally customary manner and the oxidation is carried out with, for example, benzoyl peroxide or hydrogen peroxide or with potassium permanganate (the latter only for the sulphone stage).

The formula (III) provides an unambiguous definition of the azoles additionally needed to prepare the compounds according to the invention, of the formula (I). The compounds imidazole and 1,2,4-triazole, embraced by this formula, are generally known compounds customary in laboratories.

Possible diluents for use in the preparation of the compounds according to the invention are inert organic solvents. These preferably include alcohols, such as methanol, ethanol, isopropanol or butanol, as well as nitriles, such as acetonitrile, and also ethers, such as tetrahydrofuran or dioxane and, finally, dimethylformamide.

The preparation of the compounds according to the invention is preferably carried out in the presence of bases. For this purpose, all customarily usable inorganic and organic bases may be employed. These preferentially include alkali metal carbonates, such as, for example, sodium carbonate and potassium carbonate, alkali metal hydroxides, such as, for example, sodium hydroxide, alkali metal alcoholates, such as, for example, sodium methylate, ethylate and butylate and potassium methylate, ethylate and butylate, alkali metal hydrides, such as, for example, sodium hydride and, finally, tertiary amines, such as triethylamine.

In carrying out the preparation, the reaction temperatures can be varied within a substantial range. In general, the reaction is carried out at between +40° and 180° C., preferably between 60° and 150° C.

In carrying out the process of preparation, it is preferred to employ 1 to 2 moles of azole of the formula (III) and, where appropriate, up to 1.5 moles of base per mole of oxirane of the formula (II). The end products are isolated in a generally customary manner.

The compounds of the formula (I) obtainable by the process according to the invention can be converted to acid addition salts or metal complex salts in a customary manner (in this context, compare also the data in EP-A No. 0,084,834, already cited).

Preferably, the following acids may be employed to prepare physiologically tolerated acid addition salts of the compounds of the formula (I): the hydrogen halide acids, such as, for example, hydrochloric acid and hydrobromic acid, especially hydrochloric acid, as well as phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, as well as sulphonic acids, such as, for example, p-toluenesulphonic acid and 1,5-naphthalenedisulphonic acid.

Preferably, salts of metals of main groups II to IV and of sub-groups I, II and IV to VIII of the periodic table, with copper, tin, iron and nickel being mentioned as examples, may be used to prepare metal salt complexes of the compounds of the formula (I). Suitable anions of the salts are those preferentially derived from the following acids: hydrogen halide acid, such as, for example, hydrochloric acid and hydrobromic acid, as well as phosphoric acid, nitric acid and sulphuric acid.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases included under the abovementioned main headings are mentioned below as non-limiting examples:

Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera Leucotricha;* Phytophthora species, such as, for example, *Phytophthora infestans;* Erysiphe species, such as, for example, *Erysiphe graminis;* Puccinia species, such as, for example, *Puccinia recondita;* Drechslera species, such as, for example, *Drechslera graminea* (synonym: Helminthosporium); Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example, *Xanthomonas oryzae;* Pseudomonas species, such as, for example, *Pseudomonas Lachrymans;* Pyricularia species, such as, for example, *Pyricularia oryzae;* Pellicularia species, such as, for example, *Pellicularia sasakii,* and Pyrenophora species, such as, for example, *Pyrenophora teres* (conidia form: Drechslera, synonym: Helminthosporium), Leptosphaeria species, such as, for example, *Leptosphaeria nodorum;* Cochliobolus species, such as, for example, *Cochliobolus sativus,* (conidia form: Drechslera, synonym: Helminthosporium); and Cercospora species, such as, for example, *Cercospora canescens.*

The good toleration, by plants, of the active compounds, at the concentrations required for combating plant diseases, permits treatment of above-ground parts of plants, of vegetative propagation stock and seeds, and of the soil.

The compounds are, in particular, effective against *Cochliobolus sativus* on barley, *Fusarium culmorum* on wheat, Venturia in apple cultures and Pyricularia in rice cultures. In addition, there should be mentioned a broad action as a spray and seed dressing against cereal diseases such as mildew, rust, *Pseudocercosporella herpotrichoides, Pyrenophora teres, Drechslera graminea* and *Fusarium nivale.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents: for example, non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Mineral and vegetable oils are further possible additives.

It is possible to use colorants such as inorganic pigments, for example iron oxide, titanium xide and Prussian Blue, and organic dyestuffs, such as alizarin, azo and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, slurrying, brushing on, dusting, scattering, dry dressing, moist dressing, wet dressing, slurry dressing or encrusting.

When used to treat parts of plants, the active compound concentrations in the use forms can be varied within a substantial range. They are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, amounts of active compound of 0.00001 to 0.1% by weight, preferably 0.0001 to 0.02% by weight, are required at the place of action.

PREPARATION EXAMPLES

EXAMPLE 1

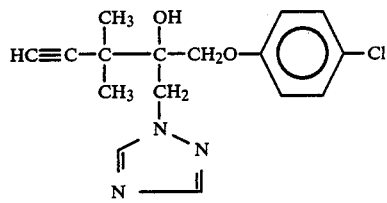

133 g (0.53 mole) of crude 2-(4-chlorophenoxymethyl)-2-(3-methyl-but-1-in-3-yl)-oxirane, dissolved in 100 ml of n-butanol, are added dropwise, with stirring, to a boiling solution of 5 g (0.052 mole) of sodium butanolate and 133 g (0.583 mole) of 1,2,4-triazole in 300 ml of n-butanol. The solution is heated to the boil for nine hours. The solvent is then distilled off in vacuo and the oily residue which remains is taken up in 500 ml of methylene chloride. The solution is washed three times with 1,000 ml of water at a time, and the organic phase is dried over sodium sulphate and then evaporated in vacuo. The oil which remains (150 g) is filtered over silica gel, with chloroform as the eluant. This gives 101 g (0.31 mole, that is to say 58.5% of theory) of 2-(4-chlorophenoxymethyl)-3,3-dimethyl-1-(1,2,4-triazol-1-yl)-pent-4-in-2-ol as colorless crystals of melting point 89°–91° C.

In addition, by use of ethyl acetate as eluant, 20.6 g (that is to say 11.9% of theory) of 2-(4-chlorophenoxymethyl)-3,3-dimethyl-1-(1,2,4-triazol-4-yl)-pent-4-in-2-ol are obtained as colorless crystals of melting point 136°–137° C.

Intermediate 1

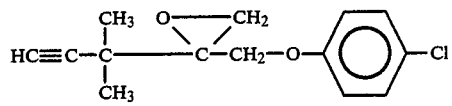

114.5 ml (1.2 moles) of dimethyl sulphate are added dropwise at between 20° and 30° C. to a solution of 56.9 ml (1.32 moles) of dimethyl sulphide in 200 ml of tert.-butanol. After 12 hours, 149 g (0.6 mole) of 1-(4-chlorophenoxy)-3,3-dimethyl-pent-4-in-2-one are added, and 134.4 g (2.4 moles) of potassium hydroxide powder are then introduced a little at a time. The mixture is left to stand for 10 hours at room temperature and 1,000 ml of water and 400 ml of toluene are then added. The organic phase is separated off, the aqueous phase is extracted twice with 200 ml of toluene at a time, and the combined toluene phases are washed three times with 1,000 ml of water at a time, dried over sodium sulphate and evaporated in vacuo. 149 g (that is to say 99% of theory) of crude 2-(4-chlorophenoxymethyl)-2-(3-methylbut-1-in-3-yl)-oxinane remain as a brownish viscous oil which can be reacted further without additional purification.

Intermediate 2

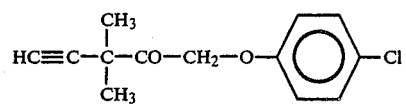

A solution of 98 g (0.67 mole) of 1-chloro-3,3-dimethyl-pent-4-in-2-one is added dropwise, with stirring, to a boiling mixture of 86.1 g (0.67 mole) of 4-chlorophenol and 92.5 g (0.67 mole) of potassium carbonate powder in 500 ml of acetone. After five hours the mixture is filtered, the filtrate is evaporated, the residue is taken up in 250 ml of methylene chloride and this solution is washed with 200 ml of 1N sodium hydroxide solution and 200 ml of water. After the solvent has been distilled off, 149 g (that is to say 94% of theory) of 1-(4-chlorophenoxy)-3,3-dimethyl-pent-4-in-2-one are obtained as a colorless viscous oil, which upon standing solidifies to crystals.

Intermediate 3

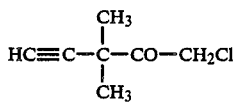

275 g (1.25 moles) of 1-chloro-3,3-dimethyl-2-phenoxy-pent-1-en-4-ine in 1.25 liters of ethanol and 620 ml of concentrated hydrochloric acid are heated for 5 hours under reflux. The mixture is diluted with water and repeatedly extracted with n-hexane. After drying the extracts and stripping off the solvent, 176 g of crude product remain. Distillation gives 149.9 g (that is to say 83% of theory) of 1-chloro-3,3-dimethyl-pent-4-in-2-one of boiling point 67°–70° C./20 mm Hg.

NMr (CDCl$_3$): 1.45 (s, 6H); 2.5 (s, 1H); 4.75 (s, 2H).

Intermediate 4

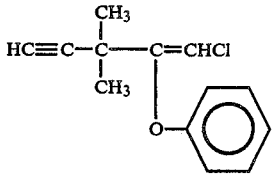

Method A:

23.2 g (0.2 mole) of sodium phenolate and 12.65 g (0.1 mole) of 1-chloro-3,3-dimethyl-penta-1,4-diine in 100 ml of absolute N,N-dimethylformamide are heated under reflux for 7 hours. The mixture is diluted with water and is repeatedly extracted with methylene chloride, and the extract is washed with dilute sodium hydroxide solution. After drying, and stripping off the solvent, 16.4 g (that is to say 74% of theory) of 1-chloro-3,3-dimethyl-2-phenoxypent-1-en-4-ine, of boiling point 85°–95° C./0.1 mm Hg, are obtained.

NMR (CDCl$_3$): 1.45 (s, 6H); 2.3 (s, 1H); 6.45 (s, 1H); 6.7–7.5 (m, 5H).

Method B:

163 g (1 mole) of 1,5-dichloro-3,3-dimethyl-pent-1-en-4-ine and 232 g (2 moles) of sodium phenolate in 1 liter of absolute N,N-dimethylformamide are heated to 140° C. in the course of 3 hours and stirring is then continued for 4 hours. The mixture is worked up as described for method A, giving 204 g of crude product, which after distillation (boiling point 0.15/87°–94° C.) gives 141 g (that is to say 64% of theory) of 1-chloro-3,3-dimethyl-2-phenoxy-pent-1-en-4-ine.

Intermediates 5 and 6

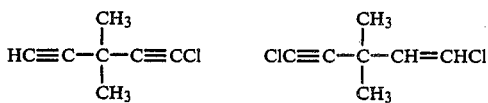

A solution of 800 g (20 moles) of NaOH in 200 ml of water is heated to 100° C. 472 g (2 moles) of 1,1,5,5-tetrachloro-3,3-dimethyl-pent-1-ene and a solution of 5 g of tetrabutylammonium bromide in 3 ml of water are added with stirring. A further four amounts of 5 g of tetrabutylammonium bromide dissolved in 3 ml of water are added at intervals of 4 hours. After 20 hours, the reaction product is isolated from the reaction mixture by steam distillation. The non-aqueous distillate and the water phase are separated and the reaction products are then isolated in a pure form by fractional distillation in vacuo, using a column. This gives 12.9 g (4% of theory) of 1,5-dichloro-3,3-dimethylpent-1-en-4-ine of boiling point 20° C./18 mm Hg and 233 g (that is to say 92% of theory) of 1-chloro-3,3-dimethylpenta-1,4-diine of boiling point 50°–52° C./18 mm Hg.

EXAMPLE 2

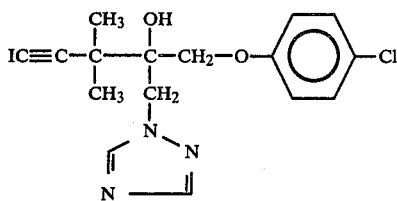

3.8 g (0.015 mole) of iodine and 7.2 ml (containing 0.072 mole of sodium hydroxide) of concentrated caustic soda solution are simultaneously stirred into a solution of 4.8 g (0.015 mole) of 2-(4-chlorophenoxymethyl)-3,3-dimethyl-1-(1,2,4-triazol-1-yl)-pent-4-in-2-ol (see Example 1) in 50 ml of methanol, in the temperature range of between 20° and 30° C. After one hour, the reaction mixture is stirred into 500 ml of water. The batch is extracted with methylene chloride and the organic phase is washed with water, dried over sodium sulphate and concentrated in vacuo. The viscous residue is taken up in diethyl ether and petroleum ether is added to the solution until it begins to turn cloudy. Trituration gives 4.0 g (that is to say 59.3% of theory) of 2-(4-chlorophenoxymethyl)-3,3-dimethyl-5-iodo-1-(1,2,4-triazol-1-yl)-pent-4-n-2-ol of melting point 108°–109° C.

The following compounds of the general formula (I)

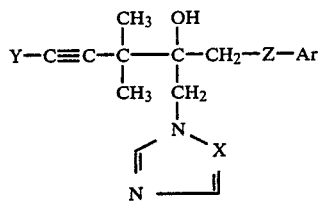

are obtained analogously to the description in Examples 1 and 2:

| Ex. No. | X | Y | Z | Ar | Physical Properties (melting point °C.) |
|---|---|---|---|---|---|
| 3 | N | H | O | 3,4-Cl₂-C₆H₃– | 144–145 |
| 4 | N | H | O | 4-biphenyl | oil |
| 5 | N | H | O | 4-F-C₆H₄– | 112–113 |
| 6 | N | H | O | 2,4-Cl₂-C₆H₃– | 117–118 |
| 7 | N | H | O | 2-Cl-C₆H₄– | 79–80 |
| 8 | N | H | O | 2-CH₃-4-Cl-C₆H₃– | oil |
| 9 | N | I | O | 2,4-Cl₂-C₆H₃– | oil |
| 10 | CH | H | O | 4-F-C₆H₄– | 97–98 |
| 11 | N | I | O | 4-F-C₆H₄– | 128–130 |
| 12 | CH | H | O | 4-Cl-C₆H₄– | 111–112 |
| 13 | CH | H | O | 4-Br-C₆H₄– | 128–129 |
| 14 | N | H | O | 4-Br-C₆H₄– | 105–106 |
| 15 | CH | H | O | 2,4-Cl₂-C₆H₃– | 139–140 |
| 16 | N | H | O | 2,4-Cl₂-C₆H₃– | 133 |
| 17 | CH | H | O | 2,4-Cl₂-C₆H₃– | Oil |
| 18 | N | H | O | 2,4-Cl₂-C₆H₃– | Oil |
| 19 | CH | I | O | 4-Cl-C₆H₄– | Oil |
| 20 | CH | I | O | 4-Br-C₆H₄– | Oil |
| 21 | N | I | O | 4-Br-C₆H₄– | 109–110 |

-continued

| Ex. No. | X | Y | Z | Ar | Physical Properties (melting point °C.) |
|---|---|---|---|---|---|
| 22 | CH | I | O | 2,4-dichlorophenyl | Oil |
| 23 | N | I | O | 2,4-dichlorophenyl | Oil |
| 24 | N | I | O | 3,4-dichlorophenyl | Oil |

The following NMR-spectroscopic data characterize those compounds according to the invention, which have been obtained as oils.

($^1$H—NMR); ppm

Example No. 4: (CDCl$_3$; 60 MHz)
1.45 (s,6H); 2.3 (s,1H); 3.95 (q,2H); 4.1 (s,1H); 4.68 (q,2H) at 6.8 (m,2H); at 7.4 (m,7H); 7.9 (s,1H); 8.15 (s,1H)

Example No. 8: (CDCl$_3$; 60 MHz)
1.45 (s,6H); 2.2 (s,3H); 2.32 (s,1H); at 3.9 (q,2H); 4.18 (s,1 4.68 (q,2H); 6.5–7.2 (3H;m); 7.9 (s,1H); 8.15 (s,1H)

Example No. 9: (CDCl$_3$; 60 MHz)
1.48 (s,6H), 3.9 (q,2H); 4.1 (s,1H); 4.75 (q,2H); 6.6–7.45 (m,3H) 7.9 (s,1H); 8.22 (s,1H)

Example No. 17: (CDCl$_3$; 80 MHz)
1.4 (d,6H); 2.35 (s,1H); at 4.2 (q,2H); 4.2 (br.s,1H); 4.9 (s,2H); 6.9–7.7 (m,6H)

Example No. 18: (CDCl$_3$; 80 MHz)
1.45 (d,6H); 2.32 (s,1H); at 4.2 (q,2H); 4.1 (br.s,1H); 4.7 (s,2H); 6.8–7.4 (m,3H); 7.9 (s,1H); 8.35 (s,1H)

Example No. 19: (CDCl$_3$; 60 MHz)
1.45 (s,6H); at 3.8 (q,2H); 4.1–4.7 (m,3H); 6.5–7.5 (m,7H)

Example No. 20: (CDCl$_3$; 60 MHz)
1.45 (s,6H); 3–4.5 (m;5H); 6.65–6.75 (m,7H)

Example No. 22: (CDCl$_3$; 60 MHz)
1.5 (s,6H); at 3.8 (q,2H); 3.6 (br.s,1H); at 4.45 (q,2H); 6.7–7.7 (m,6H)

Example No. 23: (CDCl$_3$; 60 MHz)
1.48 (s,6H); at 3.85 (q,2H); 4.1 (s,1H); at 4.75 (q,2H); 6.7–7.4 (m,3H); 7.95 (s,1H); 8.2 (s,1H)

Example No. 24: (C Cl$_3$; 60 MHz)
1.45 (d,6H); at 4.25 (q;2H); at 4.1 (m;1H); 4.7 (s;2H); 6.85–7.6 (m,3H); 7.95 (s,1H); 8.35 (s,1H)

USE EXAMPLES

The following compounds were employed as comparison substances in the use examples which follow:

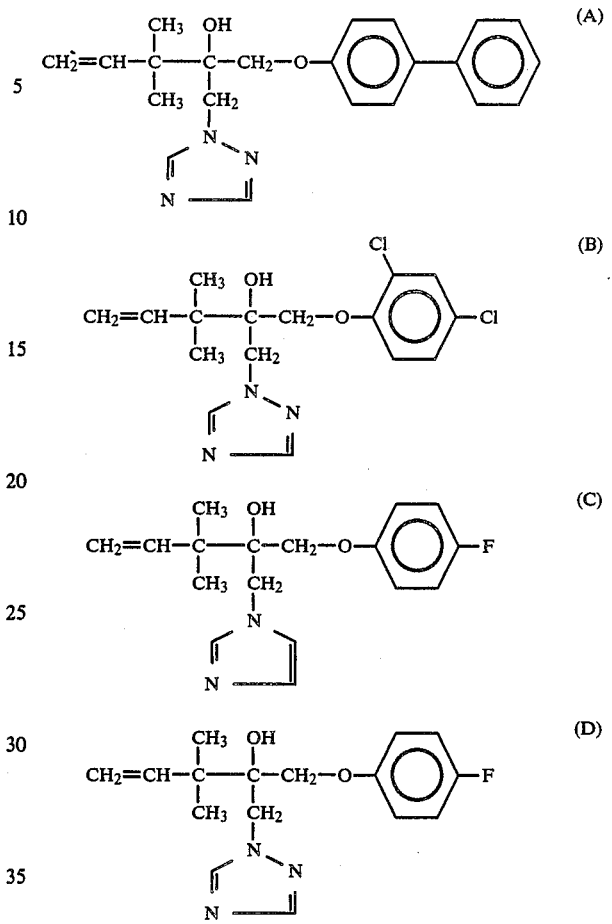

EXAMPLE A

Cochliobolus sativus test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compound according to the following preparation example: 1.

EXAMPLE B

*Fusarium culmorum* test (wheat)/seed treatment

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

2 batches of 100 grains of the wheat are sown 1 cm deep in standard soil and are cultivated in a greenhouse at a temperature of about 18° C., in seedboxes which are exposed to light for 15 hours daily.

About 3 weeks after sowing, the plants are evaluated for symptoms.

In this test, a clearly superior activity compared with the prior art is shown, for example, by the compounds according to the following preparation examples: 3, 4, 5, 2 and 1.

EXAMPLE C

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1, 3, 4, 5 and 2.

EXAMPLE D

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

A distinct superiority in activity compared to the prior art is shown in this text by, for example, the compounds according to the following preparation examples: 4, 1, 2, 6 and 7.

EXAMPLE E

Pyricularia test (rice)/systemic
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to the following preparation examples: 1, 5 and 2.

It will be understood that the specification and examples are illustrative but not limitative of the present invention and that other embodiments within the spirit and scope of the invention will suggest themselves to those skilled in the art.

We claim:

1. An azolyl-aroxymethyldimethyl-pentynol of the formula

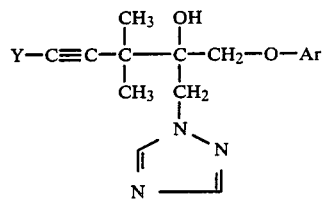

in which
Y is hydrogen or iodine, and
Ar is phenyl optionally substituted by halogen, alkyl with up to 4 carbon atoms or phenyl,
or a plant-physiologically tolerated addition product thereof with an acid or metal salt.

2. A compound or addition product according to claim 1,
in which
Ar is phenyl; or phenyl independently substituted by up to three substituents selected from the group consisting of fluorine, chlorine, methyl, ethyl, isopropyl, and phenyl.

3. A compound according to claim 1, wherein such compound is 2-(4-chlorophenoxymethyl)-3,3-dimethyl-1-(1,2,4-triazol-1-yl)-pent-4-n-2-ol of the formula

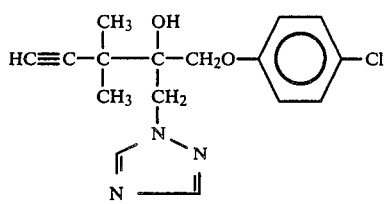

or physiologically tolerated addition product thereof with an acid or metal salt.

4. A compound according to claim 1, wherein such compound is 2-(4-biphenylyloxymethyl)-3,3-dimethyl-1-(1,2,4-triazol-1-yl)-pent-4-n-2-ol of the formula

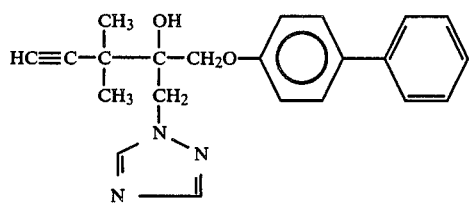

or physiologically tolerated addition product thereof with an acid or metal salt.

5. A compound according to claim 1, wherein such compound is 2-(2,4-dichlorophenoxymethyl)-3,3-dimethyl-1-(1,2,4-triazol-1-yl)-pent-4-yn-2-ol of the formula

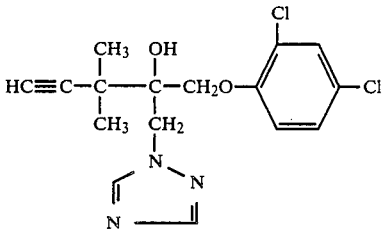

or physiologically tolerated addition product thereof with an acid or metal salt.

6. A compound according to claim 1, wherein such compound is 2-(2-chlorophenoxymethyl)-3,3-dimethyl-1-(1,2,4-triazol-1-yl)-pent-4-yn-2-ol of the formula

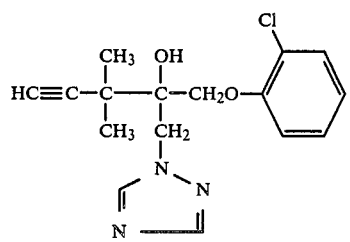

or physiologically tolerated addition product thereof with an acid or metal salt.

7. A fungicidal composition comprising a fungicidally effective amount of a compound or addition product according to claim 1 in admixture with an inert diluent.

8. A method of combating fungi which comprises applying to such fungi or to a fungus habitat a fungicidally effective amount of a compound or addition product according to claim 1.

9. The method according to claim 8, wherein such compound is
2-(4-chlorophenoxymethyl)-3,3-dimethyl-1-(1,2,4-triazol-1-yl)-pent-4-yn-2-ol,
2-(4-biphenylyloxymethyl)-3,3-dimethyl-1-(1,2,4-triazol-1-yl)-pent-4-yn-2-ol,
2-(2,4-dichlorophenoxymethyl)-3,3-dimethyl-1-(1,2,4-triazol-1-yl)-pent-4-yn-2-ol or
2-(2-chlorophenoxymethyl)-3,3-dimethyl-1-(1,2,4-triazol-1-yl)-pent-4-yn-2-ol,
or a physiologically tolerated addition product thereof with an acid or metal salt.

* * * * *

UNITED STATES PATENT AND TRADEMARK OFFICE
CERTIFICATE OF CORRECTION

PATENT NO. : 4,758,582
DATED : July 19, 1988
INVENTOR(S) : Gerhard Jäger, et al

It is certified that error appears in the above-identified patent and that said Letters Patent is hereby corrected as shown below:

| | |
|---|---|
| Title Page, "Abstract", line 9 | Correct spelling of --addition-- |
| Col. 1, lines 8, 17, 37; Col. 2, line 31 | Correct spelling of --dimethylpentynols-- |
| Col. 5, line 35 | Correct spelling of --butyn-- |
| Col. 10, lines 21, 36, 40, 55, 66; Col. 11, lines 10, 19, 37; Col. 12, lines 51, 65 | Delete " -in- " and substitute -- -yn- -- |
| Col. 10, line 66 | Correct spelling of --oxirane-- |
| Col. 11, lines 30, 59, 65; Col. 12, lines 5, 30, 32 | Delete "ine" and substitute --yne-- |
| Col. 11, line 39 | Delete "NMr" and substitute --NMR-- |
| Col. 15, line 40 | After "4.18(s,1" insert --H)-- |
| Col. 18, line 68 and Col. 19, line 23 | After "4" delete "-n-" and substitute -- -yn- -- |

Signed and Sealed this

Seventh Day of March, 1989

Attest:

DONALD J. QUIGG

Attesting Officer

Commissioner of Patents and Trademarks